US010261054B2

United States Patent
Dominguez et al.

(10) Patent No.: US 10,261,054 B2
(45) Date of Patent: Apr. 16, 2019

(54) METHOD FOR THE NON-DESTRUCTIVE ULTRASONIC TESTING OF A PART BY ECHO ANALYSIS

(71) Applicant: AIRBUS SAS, Blagnac (FR)

(72) Inventors: Nicolas Dominguez, Plaisance du Touch (FR); Frank Guibert, Toulouse (FR)

(73) Assignee: AIRBUS SAS, Blagnac (FR)

( * ) Notice: Subject to any disclaimer, the term of this patent is extended or adjusted under 35 U.S.C. 154(b) by 331 days.

(21) Appl. No.: 14/917,739

(22) PCT Filed: Sep. 9, 2014

(86) PCT No.: PCT/EP2014/069186
§ 371 (c)(1),
(2) Date: Mar. 9, 2016

(87) PCT Pub. No.: WO2015/036398
PCT Pub. Date: Mar. 19, 2015

(65) Prior Publication Data
US 2016/0223495 A1    Aug. 4, 2016

(30) Foreign Application Priority Data

Sep. 12, 2013  (FR) .................................. 13 58779

(51) Int. Cl.
*G01N 29/14* (2006.01)
*G01N 29/11* (2006.01)
(Continued)

(52) U.S. Cl.
CPC ............. *G01N 29/14* (2013.01); *G01N 29/07* (2013.01); *G01N 29/11* (2013.01); *G01N 29/30* (2013.01);
(Continued)

(58) Field of Classification Search
CPC ....................................................... G01N 29/14
(Continued)

(56) References Cited

U.S. PATENT DOCUMENTS

| 4,682,497 | A | * | 7/1987 | Sasaki | ...................... | G01H 5/00 |
| | | | | | | 73/602 |
| 2005/0277835 | A1 | * | 12/2005 | Angelsen | ................. | A61B 8/14 |
| | | | | | | 600/437 |

(Continued)

FOREIGN PATENT DOCUMENTS

| FR | 2 930 344 A1 | 10/2009 |
| JP | S55 146038 A | 11/1980 |

OTHER PUBLICATIONS

Estimating the total ultrasound attenuation along the propagation path by using a reference phantom Yassin Labyed and Timothy A. BigelowaJ Acoust Soc Am. Nov. 2010; 128(5): 3232-3238.*

(Continued)

*Primary Examiner* — Igwe U Anya
(74) *Attorney, Agent, or Firm* — Greer, Burns & Crain, Ltd.

(57) ABSTRACT

A method for the non-destructive ultrasonic testing of a part by the analysis of echoes returned by the part in response to the emission of an ultrasonic wave via an ultrasonic transducer, includes a step of determining a variable gain curve and a step of correcting the amplitude of the echoes returned by the part according to the variable gain curve and the moments of reception of the echoes. The method further includes steps of: producing a wave function representative of an ultrasonic transducer; producing transfer functions $F^m$ representative of the frequency responses of reference samples $R^m$ of the material forming the part; and calculating reference attenuation values between the wave function and the results of calculations of filtering of the wave function by (Continued)

the respective transfer functions $F^m$ of the reference samples $R^m$.

12 Claims, 4 Drawing Sheets

(51) Int. Cl.
  *G01N 29/30* (2006.01)
  *G01N 29/44* (2006.01)
  *G01N 29/46* (2006.01)
  *G01N 29/07* (2006.01)
  *G01N 29/36* (2006.01)
(52) U.S. Cl.
  CPC ......... *G01N 29/36* (2013.01); *G01N 29/4463* (2013.01); *G01N 29/46* (2013.01); *G01N 2291/011* (2013.01); *G01N 2291/015* (2013.01); *G01N 2291/044* (2013.01)
(58) Field of Classification Search
  USPC .......................................................... 702/56
  See application file for complete search history.

(56) References Cited

U.S. PATENT DOCUMENTS

2006/0052699 A1\* 3/2006 Angelsen ................. A61B 8/14
  600/437
2014/0018668 A1\* 1/2014 Zheng ................. A61B 8/4254
  600/424

OTHER PUBLICATIONS

Prediction of ultrasonic waveforms in highly attenuating plastic materials R. Kazys, L. Mazeika, R. Raiutis Prof. K. Barauskas Ultrasound Institute, Kaunas University of Technology. NDT.net May 2003, vol. 8 No. 05.\*
Hak-Joon Kim: "Transferring Distance-Amplitude Correction Curves Using Ultrasonic Modeling", AIP Conference Proceedings, vol. 700, Jan. 1, 2004 (Jan. 1, 2004), pp. 753-760, XP055121665, ISSN: 0094-243X, DOI: 10.1063/1.1711696 abstract p. 605, left-hand column Paragraph "4. Transferring DAC curves".
International Search Report, dated Nov. 18, 2014, from corresponding PCT application.

\* cited by examiner

METHOD FOR THE NON-DESTRUCTIVE ULTRASONIC TESTING OF A PART BY ECHO ANALYSIS

TECHNICAL FIELD

The present invention belongs to the field of non-destructive ultrasonic testing of a part, in particular the determination of a variable gain curve used to compensate the amplitude of ultrasound echoes returned by the part.

PRIOR ART

Non-destructive ultrasonic testing methods are used in many industrial fields. These tests are particularly important when the integrity of the parts in service must be guaranteed, notably in the case of aeronautical construction.

A non-destructive ultrasonic testing device usually includes inspection equipment and equipment for analyzing signals acquired during inspection.

The inspection equipment includes at least one ultrasound transducer that converts an electrical signal into an ultrasound signal and vice versa and an electrical signal generator/receiver that is connected to the ultrasound transducer.

The analysis equipment includes means for acquisition of the signals received from the generator/receiver and calculation means for processing the acquired signals, for example to isolate ultrasound echoes, to determine amplitude levels, etc.

In the context of ultrasonic inspection of a part, it is known to calibrate the non-destructive ultrasound test device so that, if the material forming the part is healthy, a reference reflector responds with the same amplitude, regardless of the depth at which it is located in the part, so as to provide a same-performance diagnosis in the thickness of said part. Depending on the application, such a reference reflector may be a reference defect or an element of the part itself such as the bottom face of the part, for example.

In order to carry out this equalization of the amplitude of the ultrasound echoes, it is known to determine a curve of variable amplification of the amplitude of the ultrasound echoes making it possible to compensate the loss effects (intrinsic attenuation of the material, divergence of the ultrasound field) inside a healthy material of the same type as that forming the part to be inspected. This variable gain curve is generally referred to as the time corrected gain (TCG) or distance amplitude correction (DAC) according to whether it is expressed as a function of time or of distance. The amplitude of the ultrasound echoes returned by the part can then be corrected in real time during acquisition or by post-processing the signals acquired by the acquisition means.

At present, before inspection of a part by means of an ultrasound transducer, the TCG/DAC variable gain curve is adjusted by an operator who, using said ultrasound transducer, carries out a plurality of acquisitions on a reference sample, of healthy material of the same type as that forming the part to be inspected, including a plurality of identical reference reflectors at different depths, for example artificial defects with identical dimensions.

The accuracy of the TCG/DAC variable gain curve generated in this way is limited by the number of reference reflectors in the reference sample. Moreover, establishing said TCG/DAC variable gain curve necessitates, before each inspection of a part, a plurality of ultrasound acquisitions (i.e. firings) on a reference sample, which means that establishing said TCG/DAC variable gain curve is time-consuming, and does not facilitate using and comparing results on different geographical sites (portability of the reference sample).

SUMMARY OF THE INVENTION

An objective of the present invention is to remedy some or all of the limitations of the prior art solutions, notably those explained above, by proposing a solution that makes it possible to determine, rapidly and automatically, with minimum acquisitions beforehand on a reference sample, a variable gain curve that is valid for the material forming the part and the ultrasound transducer concerned.

To this end, and in accordance with a first aspect, the invention concerns a method of non-destructive ultrasonic testing of a part by analysis of echoes returned by said part in response to the emission of an ultrasound wave by means of an ultrasound transducer, said method including a step of determination of a variable gain curve and a step of correction of the amplitude of the echoes returned by the part as a function of the variable gain curve and of the times of reception of said echoes, characterized in that said method includes steps of:

- obtaining a wave function representing the frequency spectrum of the ultrasound waves emitted by the ultrasound transducer,
- obtaining transfer functions $F^m$ representing the frequency responses of reference samples $R^m$ of the material forming said part, with respective different thicknesses $e_m$,
- calculating reference attenuation values between on the one hand the wave function and on the other hand the results of calculations that filter said wave function by the respective transfer functions $F^m$ of the reference samples $R^m$, the variable gain curve being determined as a function of the reference attenuation values.

This makes it possible to reduce the duration of the inspection of the part and more particularly to reduce the time necessary for establishing the variable gain curve.

In actual fact, in accordance with the prior art, the variable gain curve is established as a function of reference attenuation values calculated as a function of signals measured during real inspections of reference samples. In accordance with the invention, the reference attenuation values are calculated as a function of simulated signals, notably obtained by calculations that filter the wave function by the transfer functions, which amounts to carrying out virtual inspections of reference samples.

In particular embodiments, the method in accordance with the invention may further include one or more of the following features, separately or in all technically possible combinations.

In one particular embodiment, the wave function is obtained from a database in which said wave function was stored beforehand. This makes it possible to accelerate the establishing of the variable gain curve in that the step of obtaining the wave function consists in reading said function in the database.

In one particular embodiment, the wave function is estimated by measuring an ultrasound wave emitted by the ultrasound transducer into a coupling medium in the absence of said part or reference sample.

In one particular embodiment, the transfer functions $F^m$ are obtained from a database in which said transfer functions have been stored beforehand and/or calculated on the basis of at least one reference transfer function obtained from a database in which said reference transfer function has been stored beforehand. This makes it possible to accelerate the establishing of the variable gain curve in that the step of obtaining the transfer functions consists in reading said transfer functions in the database and/or reading the at least one reference transfer function in the database followed by numerical calculation of said transfer functions.

In one particular embodiment, the method includes a step of measuring:
- a frequency spectrum $S_R$ of an ultrasound wave that has passed through a real reference sample $R_R$ of thickness $d_R$ made of a healthy material of the same type as that of the part,
- a frequency spectrum S of an ultrasound wave with the same characteristics that has not passed through said real reference sample $R_R$, wherein the transfer function $F^m$ of the reference sample $R^m$ of thickness $e_m$ is determined in the frequency domain by calculating for discrete frequency values f the expression:

$$F^m(f) = \exp\left(\frac{e_m}{a \cdot d_R}\right) \cdot \frac{|S_R(f)|}{A \cdot |S(f)|},$$

in which expression a and A are positive factors.

This makes it possible to minimize the requirement to inspect reference samples in that a plurality of transfer functions $F^m(f)$ are calculated from frequency spectra S(f) and $S_R(f)$ measured for a single real reference sample.

Advantageously, to reduce the quantity of data that must be stored, the transfer function $F^m$ of the reference sample $R^m$ of thickness $e_m$ is determined in accordance with the expression:

$$F^m(f) = \exp\left(-\frac{a_R(f) \cdot e_m}{20}\right),$$

wherein $\alpha_R(f)$ is a reference transfer function determined in accordance with the expression:

$$a_R(f) = \frac{1}{a \cdot d_R} 20 \cdot \log\left(\frac{A \cdot |S(f)|}{|S_R(f)|}\right).$$

In one particular embodiment, the method includes a step of estimating the propagation speed of the ultrasound waves in the part and:
- the amplitude of the echoes returned by the part is corrected as a function of the variable gain curve, the times of reception of said echoes and the propagation speed of the ultrasound waves in said part, or
- the variable gain curve is determined as a function of the reference attenuation values and the propagation speed of the ultrasound waves in said path.

DESCRIPTION OF THE FIGURES

The invention will be better understood on reading the following description, given by way of nonlimiting example, and with reference to the figures, which show.

In these figures, references identical from one figure to another designate identical or analogous elements. For reasons of clarity, the elements represented are not to scale, unless otherwise indicated.

DETAILED DESCRIPTION OF EMBODIMENTS

Figure 1:
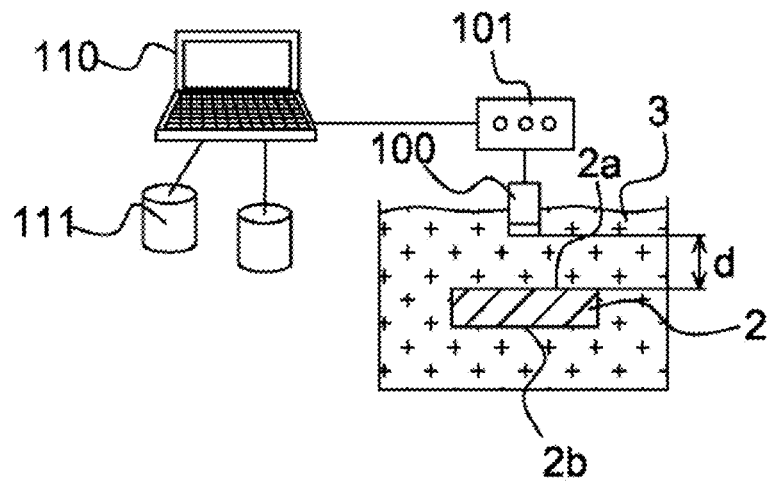
FIG. 1: a diagram representing a non-destructive ultrasonic testing device in accordance with the invention.

As represented in FIG. 1, a method 6 of non-destructive ultrasonic testing of a part 2 employs ultrasound inspection equipment, notably an ultrasound transducer 100 and a generator/receiver 101 of signals, generally electrical signals, and equipment for the analysis of data collected during the inspection, such as calculation means 110 (a microcontroller, a computer including a microprocessor, etc) and storage means 111 (an electronic and/or magnetic memory, etc) for storing the results of the ultrasound inspection.

In the known manner, during non-destructive ultrasonic testing the part 2 is at least partly immersed in a coupling medium 3 consisting of water or of gel.

The transducer 100 is generally placed so as to emit ultrasound waves with substantially normal incidence on a front face 2a of the part.

The transducer 100 from FIG. 1 is used to emit and to receive and measures ultrasound echoes caused by acoustic impedance discontinuities.

A so-called "front" echo or "entry echo" is received for an interface between the front face 2a of the part 2 and the coupling medium 3 and a so-called "back" echo is generally received for an interface between said coupling medium and a rear face 2b of said part, situated on the side of the part opposite the transducer 100.

In the remainder of the description, the following notation is used for the representation of functions in the frequency and time domains: a function denoted H may correspond to one or the other of the representations, H(f) is the frequency domain representation of the function H and H(t) is the time domain representation of said function H.

Figure 2:
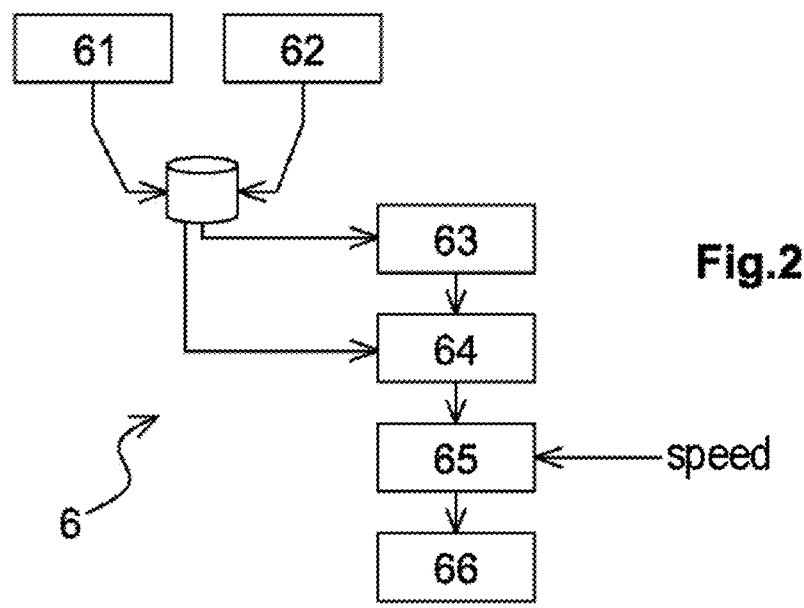
FIG. 2: a diagram representing the steps of a method in accordance with the invention of determining a variable gain curve with the propagation time of an ultrasound wave in the material forming the part.

FIG. 2 represents the principal steps 61, 62, 63, 64, 65 and 66 of a preferred embodiment of the non-destructive testing method 6. In particular, the step 65 corresponds to the determination of a variable gain curve used in the step 66 to correct the amplitude of the ultrasound echoes returned by the part 2. In the remainder of the description, the nonlimiting situation is that of seeking to establish a variable gain curve making it possible to equalize the amplitude of the back echo. As indicated above, the invention may nevertheless be applied considering other types of reference reflectors, for example to determine a variable gain curve making it possible to equalize the amplitude of the ultrasound echoes returned by reference defects.

The results of some steps are reproducible and, if said results are stored in order to be reused said steps are not necessarily executed again.

In step 61 of the method 6, the ultrasound transducer 100 is characterized.

Figure 3:
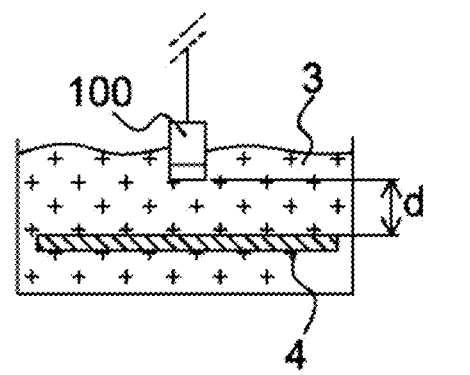
FIG. 3: a diagram representing a method of determining a wave function of an ultrasound transducer.

Characterizing the transducer 100 consists in determining a wave function $F_o$ representing the frequency spectrum of the ultrasound waves emitted by said transducer and received in the absence of the part. The wave function $F_o$ is for example determined by placing a reflective plate 4 in front of the transducer 100 in the coupling medium 3, as represented in FIG. 3, and measuring the echo of an ultrasound wave reflected by the reflective plate 4.

The reflective plate 4 is preferably placed at a distance d from the transducer 100 substantially equal to the distance used for the non-destructive testing of the part 2, notably in the case of a focused ultrasound transducer.

Figure 4:
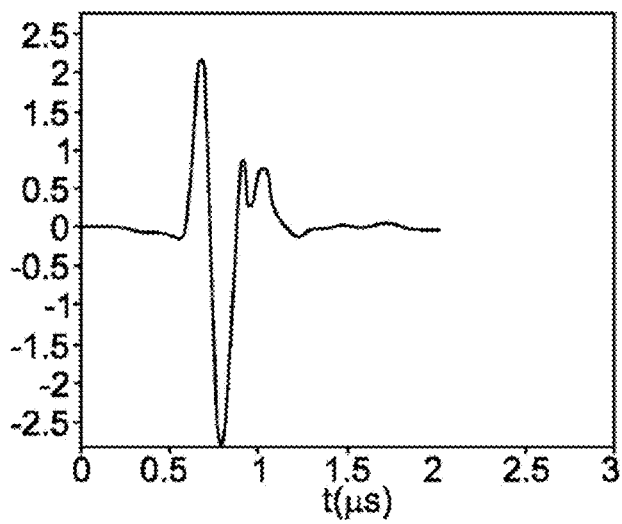
FIG. 4: an example of a wave function in the time domain.

An example of a measured echo is represented in FIG. 4. Such an echo is a temporal representation $F_o(t)$ of the wave function $F_o$ associated with the transducer 100.

Figure 5:
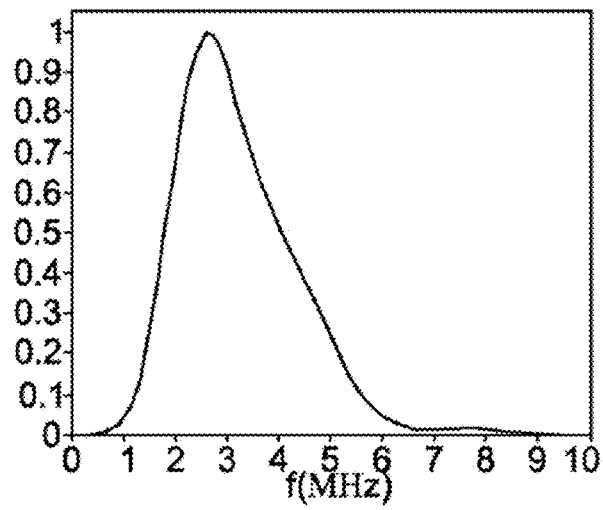
FIG. 5: an example of a wave function in the frequency domain.

The wave function $F_o(t)$ is preferably transposed into the frequency domain, for example by means of a Fourier transform, in order to have a wave function $F_o(f)$ directly in the form of a frequency spectrum. The frequency spectrum associated with the echo represented in FIG. 4 is represented in FIG. 5.

The frequencies f considered for the wave function $F_o(f)$ are preferably discrete values in a range $[f_{MIN}, f_{MAX}]$. The range $[f_{MIN}, f_{MAX}]$ is chosen so that most of the power of the ultrasound waves emitted by each ultrasound transducer that can be used lies within said range. In the FIG. 5 example, $f_{MIN}=0$ Hz and $f_{MAX}=10$ MHz.

The wave function $F_o$ associated with the transducer 100 depends only on the transducer 100 and does not depend on the part 2 to be tested.

The wave function associated with the transducer 100 is therefore preferably stored in the database in order to be reused to determine a variable gain curve for parts other than the part 2 by means of the same transducer 100. In this case, if the wave function $F_o$ has been established beforehand and stored in the database, step 61 is not necessarily executed, except substantially periodically, for example, to take into account the evolution over time of the characteristics of the transducer 100. The database preferably stores a plurality of wave functions $F_o1$, $F_o2$, $F_o3$, etc. corresponding to different ultrasound transducers liable to be used for inspecting parts. The database may also include, associated with the same ultrasound transducer, a plurality of wave functions corresponding to different possible values of the test distance d.

Such a database makes it possible to save time in using the non-destructive testing method 6 by not executing the step 61 of characterizing the ultrasound transducer when the corresponding wave function is already known and stored in the database.

During step 62 a healthy material of the same type as the material forming the part 2 is characterized. For example, this characterization is effected by inspecting at least one real reference sample $R_R$ made from said healthy material so as to obtain at least one reference transfer function $\alpha_R$ representing the frequency response of said real reference sample.

The at least one reference transfer function $\alpha_R$ is determined by emitting ultrasound waves in the direction of the real reference sample $R_R$ using an ultrasound transducer (or two transducers in the case of an inspection by transmission).

The at least one reference transfer function $\alpha_R$ is determined for example from a frequency spectrum $S(f)$ of an ultrasound wave that has not passed through the real reference sample $R_R$ and a frequency spectrum $S_R(f)$ of an ultrasound wave that has passed through said real reference sample which are preferably measured over the range $[f_{MIN}, f_{MAX}]$ described above.

Figure 6:
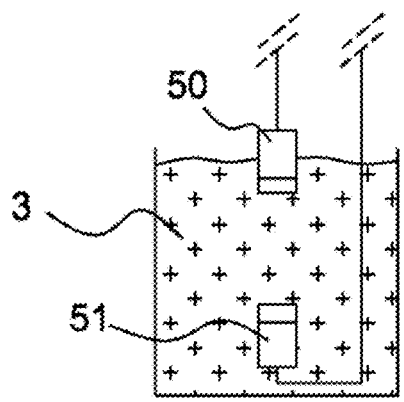
FIGS. 6 and 7: a diagram representing a method of characterizing a real reference sample $R_R$.
Figure 7:
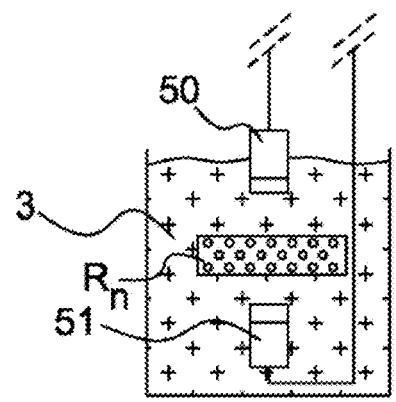

In the case of a measurement of the frequency spectra by transmission, as represented in FIGS. 6 and 7, using an emitting transducer 50 and a receiving transducer 51, the frequency spectrum $S(f)$ is measured without the real reference sample $R_R$ represented in FIG. 6 and the frequency spectrum $S_R(f)$ is measured with said reference sample inserted between the transducers 50 and 51 represented in FIG. 7.

In a preferred embodiment, the reference transfer function $\alpha_R$ is determined by calculating the following expression for each frequency f concerned in the range $[F_{MIN}, F_{MAX}]$:

$$a_R(f) = \frac{1}{d_R} 20 \cdot \log\left(\frac{T \cdot |S(f)|}{|S_R(f)|}\right)$$

in which expression T is a transmission coefficient taking account of the losses at the interfaces corresponding to a front face and a rear face of the real reference sample $R_R$.

The coefficient T, the value of which is either calculated or measured, is equal to the following expression:

$$T = \frac{4 Z_{MC} \cdot Z_{CO}}{(Z_{MC} + Z_{CO})^2}$$

where $Z_{MC}$ is the acoustic impedance of the coupling medium and $Z_{CO}$ is the acoustic impedance of the material.

In the case of an inspection by double transmission of the real reference sample $R_R$, that is to say in a set-up with a transducer and a mirror as in FIG. 3, the reference transfer function $\alpha_R(f)$ is for example calculated according to the expression:

$$a_R(f) = \frac{1}{2 \cdot d_R} 20 \cdot \log\left(\frac{T^2 \cdot |S(f)|}{|S_R(f)|}\right)$$

In actual fact, because of the double transmission through the real reference sample $R_R$, the transmission coefficient T and the thickness $d_R$ of said reference sample must be taken into account twice.

The reference transfer function $\alpha_R(f)$ can also be calculated by other methods, for example by comparing a frequency spectrum of the front echo and a frequency spectrum of the back echo returned by the real reference sample, and it is understood that the calculation of said attenuation function is not limited to the methods described. More generally, the reference transfer function $\alpha_R(f)$ is calculated in accordance with the expression:

$$a_R(f) = \frac{1}{a \cdot d_R} 20 \cdot \log\left(\frac{A \cdot |S(f)|}{|S_R(f)|}\right)$$

where a and A are real factors that depend on the inspection method used to measure the frequency spectra $S(f)$ and $S_R(f)$ (a=1 and A=T for an inspection by transmission, a=2 and A=T² for an inspection by double transmission).

In this form, the reference transfer function $\alpha_R$ corresponds to a frequency response per unit length and can easily be used to calculate transfer functions $F^m$ for (virtual) reference samples $R_m$ of arbitrary thickness $e_m$ in accordance with the following expression:

$$F^m(f) = \exp\left(-\frac{a_R(f) \cdot e_m}{20}\right).$$

The transfer function $F^m(f)$ can also be calculated directly from the frequency spectra $S(f)$ and $S_R(f)$, and whether said reference transfer function is calculated or not depends on the embodiment chosen. The transfer function $F^m(f)$ is for example determined directly in accordance with the following general expression:

$$F^m(f) = \exp\left(\frac{e_m}{ad_R}\right) \cdot \frac{|S_R(f)|}{A|S(f)|}.$$

Figure 8:
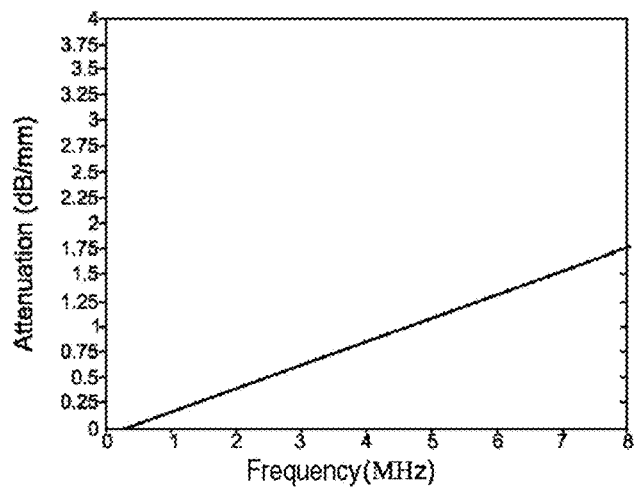
FIG. 8: an example of a reference attenuation function in accordance with the invention.
Figure 9:
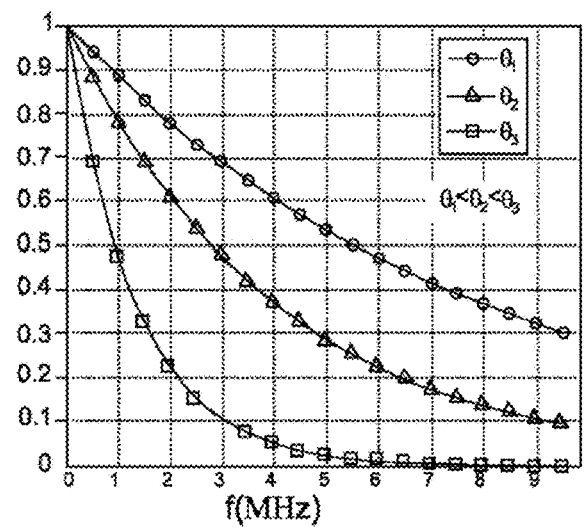
FIG. 9: an example of a transfer function in accordance with the invention.

A reference transfer function $\alpha_R(f)$ is represented in FIG. 8 and transfer functions $F^m$ for reference samples $R^m$ of thickness $e_m$ are represented in FIG. 9.

It is to be noted that the reference transfer function $\alpha_R$ and the transfer functions $F^m$ do not depend on the ultrasound transducer used but only on the characteristics of the real reference samples $R_R$. Like the wave function $F_o$, the reference transfer function or functions $\alpha_R$ and/or the transfer functions $F^m$ are preferably stored in a database to be reused. Accordingly, for a given healthy material, the characterization step 62 for which at least one real reference sample $R_R$ is inspected does not have to be executed again for subsequent inspections of parts made from the same healthy material. The database preferably stores a plurality of reference transfer functions $\alpha_R$ and/or transfer functions $F^m$ corresponding to different types of healthy materials.

Step 63 of the non-destructive testing method 6 corresponds to a step of obtaining transfer functions $F^m$ for reference samples $R^m$ for different thicknesses $e_m$ (1≤m≤M) matching the thickness of the part 2 to be tested. More particularly, the thicknesses $e_m$ considered are advantageously equal to or less than the thickness of the part 2. If the transfer functions $F^m$ associated with such thicknesses $e_m$ equal to or less than the thickness of the part 2 are to be found in the database, step 63 consists in reading said transfer functions $F^m$ in said database. If not, said transfer functions $F^m$ are for example calculated on the basis of the reference transfer function $\alpha_R$ stored beforehand in the database.

In step 64 of the non-destructive testing method 6 reference attenuation values are calculated using the reference samples $R^m$ of thickness $e_m$ the transfer functions $F^m$ of which were obtained during step 63. Said reference attenuation values are calculated using the wave function $F_o$ characteristic of the transducer 100, obtained from the database, and the transfer functions $F^m$(1≤m≤M) characteristic of the reference samples $R^m$ of thickness $e_m$.

To simulate the attenuation of ultrasound waves from the transducer 100 by the reference sample $R^m$ of thickness $e_m$ the wave function $F_o$ associated with the transducer 100 is filtered by the transfer function $F^m$. In the known manner, the filtering is calculated in the time domain or the frequency domain. In the case of filtering calculated in the frequency domain, the product $F^m(f) \cdot F_o(f)$ of the transfer function by the wave function is calculated for each frequency f considered in the range $[f_{MIN}, f_{MAX}]$.

Figure 10:
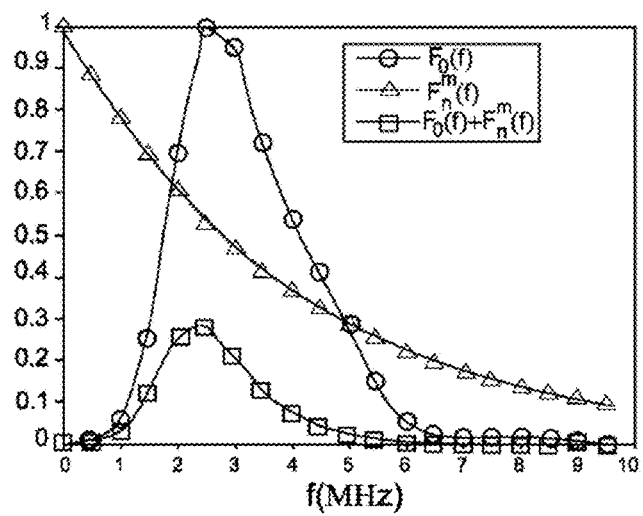
FIGS. 10 and 11: an example of filtering a wave function by a transfer function in the frequency and time domains.
Figure 11:
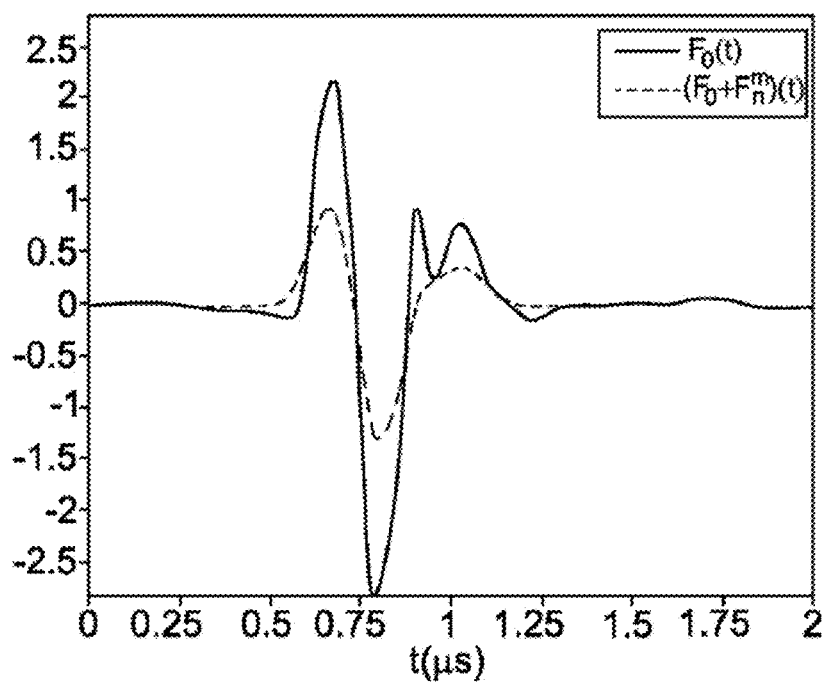

An example illustrating the filtering calculation in the frequency domain is represented in FIG. 10. The result $F^m(f) \cdot F_o(f)$ of the filtering calculation in the time domain is represented in FIG. 11.

A reference attenuation value is calculated for each reference sample $R^m$ (1≤m≤M), for example by calculating the ratio of the powers of the wave function $F_o$ before and after filtering, said powers being calculated by integrating the frequency spectra $F_o(f)$ and $F^m(f) \cdot F_o(f)$. A different calculation method estimates the reference attenuation value in the time domain by calculating a ratio of the extreme values of the wave function $F_o(t)$ before and after filtering.

Figure 12:
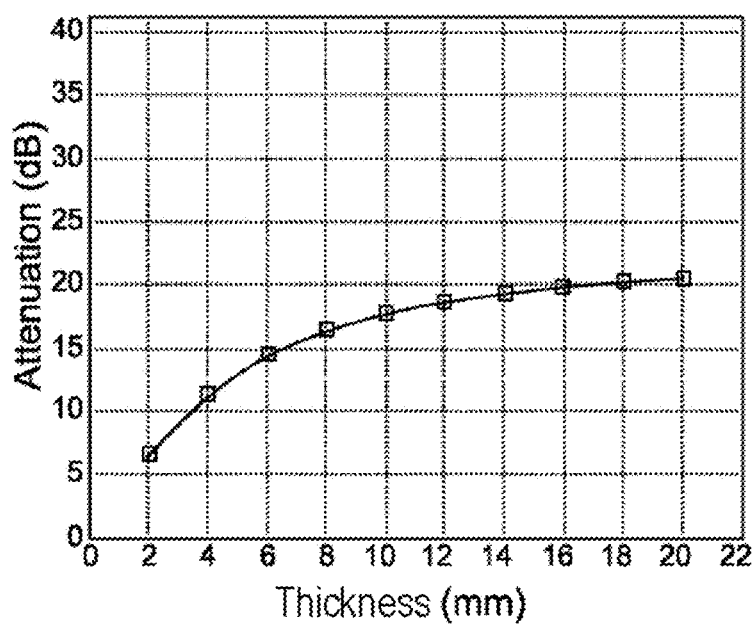
FIG. 12: examples of methods in accordance with the invention of representing reference attenuation values.

In FIG. 12 reference attenuation values are represented as a function of different thicknesses.

In step 65, the variable gain curve is determined as a function of the reference attenuation values determined in step 64. In the example illustrated by FIG. 2, the TCG variable gain curve expressed as a function of time and consequently also determined as a function of an estimate of the propagation speed of the ultrasound waves in the part 2 in order to convert the thicknesses $e_m$ into propagation times.

In step 66, and therefore when the TCG variable gain curve has been determined, the part 2 is inspected and the amplitude of the ultrasound echoes returned by the part 2 is corrected as a function of said TCG variable gain curve and the times of reception of said ultrasound echoes. The amplitude of the ultrasound echoes returned by the part 2 may be corrected in real time during inspection or by post-processing the signals acquired during inspection. Because of this correction, the back echo will have the same amplitude as the entry echo if the material of the part 2 is healthy.

In the case of a DAC variable gain curve, the estimate of the propagation speed of the ultrasound waves in the part 2 is used during the correction process in order to convert the times of reception of the ultrasound echoes into distances traveled.

The foregoing description clearly shows that by virtue of its various features and their advantages the present invention achieves the objectives set for it. In particular, the present invention makes it possible to determine a variable gain curve in a simple and rapid manner thanks to the determination of the reference attenuation values by numerical simulation rather than by real inspection of reference samples, reusing wave functions and transfer functions stored in a database.

The invention claimed is:

1. A method (6) of non-destructive ultrasonic testing of a part (2) comprising:
   emitting an ultrasound wave by means of an ultrasound transducer (100) with substantially normal incidence of a front face (2a) of the part (2), and
   analyzing echoes returned by said part (2) in response to said emission of said ultrasound wave,
   wherein said analyzing echoes comprises:
      determining a variable gain curve, and
      correcting the amplitude of the echoes returned by the part (2) as a function of the variable gain curve and of the times of reception of said echoes, wherein said determining a variable gain curve includes steps of:
         obtaining a wave function representing the frequency spectrum of the ultrasound waves emitted by the ultrasound transducer (100), obtaining transfer functions $F^m$ representing the frequency responses of reference samples $R^m$ of the material forming said part, with respective different thicknesses $e_m$, calculating reference attenuation values between on the one hand the wave function and on the other hand the results of calculations that filter said wave function by the respective transfer functions $F^m$ of the reference samples $R^m$, the variable gain curve being determined as a function of the reference attenuation values, wherein the wave function is estimated by measuring an ultrasound wave emitted by the ultrasound transducer (100) into a coupling medium (3) in the absence of said part (2) or reference sample, wherein said obtaining transfer functions comprises:

measuring a frequency spectrum $S_R$ of an ultrasound wave that has passed through a real reference sample $R_R$ of thickness $d_R$ made of a healthy material of the same type as that of the part (2), and measuring a frequency spectrum $S$ of an ultrasound wave with the same characteristics that has not passed through said real reference sample $R_R$.

2. The method (6) as claimed in claim 1, wherein the wave function is obtained from a database in which said wave function has been stored beforehand.

3. The method (6) as claimed in claim 2, wherein the wave function is estimated by measuring an ultrasound wave emitted by the ultrasound transducer (100) into a coupling medium (3) in the absence of said part (2) or reference sample.

4. The method (6) as claimed in claim 2, wherein the transfer functions $F^m$ are obtained from a database in which said transfer functions have been stored beforehand and/or calculated on the basis of at least one reference transfer function obtained from a database in which said reference transfer function has been stored beforehand.

5. The method (6) as claimed in claim 2, wherein the transfer function $F^m$ of the reference sample Rm of thickness $e_m$ is determined in the frequency domain by calculating for discrete frequency values f the expression:

$$F^m(f) = \exp\left(\frac{e_m}{a \cdot d_R}\right) \cdot \frac{|S_R(f)|}{A \cdot |S(f)|},$$

in which expression a and A are positive factors.

6. The method (6) as claimed in claim 1, wherein the transfer functions $F^m$ are obtained from a database in which said transfer functions have been stored beforehand and/or calculated on the basis of at least one reference transfer function obtained from a database in which said reference transfer function has been stored beforehand.

7. The method (6) as claimed in claim 6, wherein the transfer function $F^m$ of the reference sample $R^m$ of thickness $e_m$ is determined in the frequency domain by calculating for discrete frequency values f the expression:

$$F^m(f) = \exp\left(\frac{e_m}{a \cdot d_R}\right) \cdot \frac{|S_R(f)|}{A \cdot |S(f)|},$$

in which expression a and A are positive factors.

8. The method (6) as claimed in claim 1, wherein the transfer function $F^m$ of the reference sample Rm of thickness $e_m$ is determined in the frequency domain by calculating for discrete frequency values f the expression:

$$F^m(f) = \exp\left(\frac{e_m}{a \cdot d_R}\right) \cdot \frac{|S_R(f)|}{A \cdot |S(f)|},$$

in which expression a and A are positive factors.

9. The method (6) as claimed in claim 8, wherein the transfer function $F^m$ of the reference sample $R^m$ of thickness $e_m$ is determined in accordance with the expression:

$$F^m(f) = \exp\left(-\frac{a_R(f) \cdot e_m}{20}\right),$$

wherein $\alpha_R(f)$ is a reference transfer function determined in accordance with the expression:

$$a_R(f) = \frac{1}{a \cdot d_R} 20 \cdot \log\left(\frac{A \cdot |S(f)|}{|S_R(f)|}\right).$$

10. The method (6) as claimed in claim 1, including a step of estimating the propagation speed of the ultrasound waves in the part (2), and wherein:

the amplitude of the echoes returned by the part (2) is corrected as a function of the variable gain curve, the times of reception of said echoes and the propagation speed of the ultrasound waves in said part, or the variable gain curve is determined as a function of the reference attenuation values and the propagation speed of the ultrasound waves in said path.

11. The method (6) as claimed in claim 1, wherein the transfer functions $F^m$ are obtained from a database in which said transfer functions have been stored beforehand and/or calculated on the basis of at least one reference transfer function obtained from a database in which said reference transfer function has been stored beforehand.

12. The method (6) as claimed in claim 1, wherein the transfer function $F^m$ of the reference sample $R^m$ of thickness $e_m$ is determined in the frequency domain by calculating for discrete frequency values f the expression:

$$F^m(f) = \exp\left(\frac{e_m}{a \cdot d_R}\right) \cdot \frac{|S_R(f)|}{A \cdot |S(f)|},$$

in which expression a and A are positive factors.

* * * * *